United States Patent
Yun et al.

(10) Patent No.: US 7,494,761 B2
(45) Date of Patent: Feb. 24, 2009

(54) CYCLODEXTRIN DERIVATIVE, PHOTORESIST COMPOSITION INCLUDING THE CYCLODEXTRIN DERIVATIVE AND METHOD OF FORMING A PATTERN USING THE PHOTORESIST COMPOSITION

(75) Inventors: Hyo-Jin Yun, Anyang-si (KR); Young-Gil Kwon, Yongin-si (KR); Young-Ho Kim, Yongin-si (KR); Hong Lee, Suwon-si (KR); Do-Young Kim, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 11/853,047

(22) Filed: Sep. 11, 2007

(65) Prior Publication Data
US 2008/0070157 A1    Mar. 20, 2008

(30) Foreign Application Priority Data
Sep. 14, 2006   (KR) ............... 10-2006-0088827

(51) Int. Cl.
*G03F 7/004* (2006.01)
*G03F 7/30* (2006.01)
*C08B 31/00* (2006.01)

(52) U.S. Cl. ............ 430/270.1; 430/326; 430/330; 430/911; 514/58; 536/103

(58) Field of Classification Search ........ 430/270.1, 430/326, 330, 926; 514/58; 536/103
See application file for complete search history.

(56) References Cited

U.S. PATENT DOCUMENTS

| 5,824,451 | A | * | 10/1998 | Aoai et al. .............. 430/270.1 |
| 5,994,031 | A | * | 11/1999 | Hirai et al. ................ 430/302 |
| 5,998,084 | A | * | 12/1999 | Elsaesser et al. ........... 430/165 |
| 2005/0252628 | A1 | * | 11/2005 | Day et al. ................... 162/158 |

FOREIGN PATENT DOCUMENTS

| JP | 2002-169291 | 6/2002 |
| JP | 2005-306917 | 11/2005 |
| JP | 2005-308827 | 11/2005 |

OTHER PUBLICATIONS

Trotta, Francesco, Moraglio, Giovanni, Zerbinati, Orfeo, Nonnato, Antonello, "Alkyl Capped Carbonates of beta-Cyclodextrin" Journal of Inclusion Phenomena and Molecular Recognition in Chemistry 23 (1996): 269-276.*

* cited by examiner

*Primary Examiner*—John S Chu
(74) *Attorney, Agent, or Firm*—Volentine & Whitt, PLLC (57) ABSTRACT

A photoresist film is formed on an object layer of a semiconductor device by coating the object layer with a photoresist composition including about 7 percent to about 14 percent by weight of a cyclodextrin derivative, about 0.1 percent to about 0.5 percent by weight of a photoacid generator, and a remainder of an organic solvent. The cyclodextrin derivative includes a $\beta$-cyclodextrin moiety and at least one alkyl carbonate group.

11 Claims, 3 Drawing Sheets

CYCLODEXTRIN DERIVATIVE, PHOTORESIST COMPOSITION INCLUDING THE CYCLODEXTRIN DERIVATIVE AND METHOD OF FORMING A PATTERN USING THE PHOTORESIST COMPOSITION

CROSS-REFERENCE TO PRIORITY APPLICATION

A claim of priority is made to Korean Patent Application No. 10-2006-0088827, filed on Sep. 14, 2006, the subject mater of which is hereby incorporated by reference.

CROSS-REFERENCE TO RELATED APPLICATION

This application is related to co-pending U.S. patent application Ser. No. 11/853,075 to Hyo-Jin Y U N et al., entitled "Inclusion Complex, Photoresist Composition Having the Inclusion Complex and Method of Forming a Pattern Using the Photoresist Composition", which claims priority of Korean Patent Application No. 10-2006-0088826 (filed on Sep. 14, 2006), the subject matter of which is hereby incorporated by reference.

BACKGROUND OF THE INVENTION

1. Field of the Invention

The present invention relates to forming a pattern using a photoresist composition including a cyclodextrin derivative. More particularly, example embodiments of the present invention relate to a cyclodextrin derivative, a photoresist composition including the cyclodextrin derivative, and a method of forming a semiconductor device pattern using the photoresist composition.

2. Description of the Related Art

Recently, semiconductor device technology has rapidly advanced, as information media, such as personal computers, have become more widely used. Semiconductor devices are required to operate at very high speeds and to have large storage capacities. To meet recent industry trends, the manufacturing technologies of semiconductor devices have been developed to improve integration, reliability and response speeds of the semiconductor devices. In particular, a fine processing technology, such as photolithography, has enabled stricter requirements to be met, improving the degree of integration of semiconductor devices.

To fabricate a semiconductor device, a chemical amplification type photoresist composition is used in the photolithography process in order to form a photoresist pattern utilized as an etching mask. The photoresist composition is prepared by mixing a photoacid generator for generating an acid material, a polymer for sensitively reacting with the acid material, and a solvent. The photoresist composition has a variable solubility in a developing solution, which is changed in accordance with a light exposure operation. Accordingly, the photoresist pattern having a determined shape may be acquired by coating a surface of a substrate with the photoresist composition, partially exposing a photoresist film to light, and sequentially developing the exposed portions of the photoresist film.

A photoresist composition, including a polymer having a high molecular weight, has been conventionally used for forming a photoresist pattern. As a pattern in a semiconductor device becomes finer, a line width of the photoresist pattern is reduced to a molecular size of the polymer. The polymer has various molecular weights and various sizes, as well as an entangled structure. When a photoresist composition including the polymer is developed, molecules of the polymer are swollen in a developing solution, and are not dissolved in the developing solution at a constant rate. Thus, a resolution of the photoresist pattern is reduced and a line width roughness of the photoresist pattern deteriorates.

When a semiconductor device has a 240 nm dimension, a deviation of the line width roughness in a photoresist pattern is at most about 20 nm, which is about 16 percent of a line width based on both edges of the line. Thus, the deviation of the line width is inevitably generated in the method for fabricating a semiconductor device. However, as a semiconductor device having a 90 nm dimension is developed, the deviation of the line width roughness is increased to about 22 percent of the line width. When a semiconductor device has a dimension less than about 70 nm, the deviation of the line width roughness is increased to more than about 29 percent.

In order to improve the photoresist composition, a molecular weight of a polymer included in a photoresist composition has been adjusted or a type of a de-blocking group of the polymer has been changed. However, photoresist compositions having an adjusted molecular weight or a changed de-blocking group still result in great loss of a photoresist pattern in a developing process and a deterioration of mechanical properties of the polymer included in the photoresist composition. This is because a molecular size of the polymer applied to the photoresist composition is not considered.

SUMMARY OF THE INVENTION

An aspect of the present invention provides a cyclodextrin derivative for a photoresist that includes a β-cyclodextrin moiety and at least one alkyl carbonate group. The cyclodextrin derivative may have a chemical structure represented by Formula (1), in which $R_1$ represents an alkyl group having 1 to 10 carbon atoms.

Formula (1)

The cyclodextrin derivative may be prepared by combining β-cyclodextrin represented by Formula (2) with a tert-alkyl carbonate represented by Formula (3), in which each of $R_2$, $R_3$ and $R_4$ independently represents an alkyl group having 1 to 3 carbon atoms.

Formula (2)

-continued

Formula (3)

Further, the cyclodextrin derivative may be prepared by reacting β-cyclodextrin with di-tert-butyl dicarbonate represented by Formula (4) in an organic solvent.

Formula (4)

Another aspect of the present invention provides a photoresist composition that includes about 7 percent to about 14 percent by weight of a cyclodextrin derivative represented by the Formula (1), about 0.1 percent to about 0.5 percent by weight of a photoacid generator, and an organic solvent, which may be the remainder percentage by weight. The cyclodextrin derivative may be prepared by combining β-cyclodextrin represented by Formula (2) with a tert-alkyl carbonate represented by Formula (3). Also, the cyclodextrin derivative may be prepared by reacting β-cyclodextrin with di-tert-butyl dicarbonate represented by Formula (4) in the organic solvent.

The photoacid generator may include at least one selected from the group of a triarylsulfonium salt, a diaryliodonium salt, a sulfonate and N-hydroxysuccinimide triflate. The organic solvent may include at least one selected from the group of ethylene glycol monomethyl ether, ethylene glycol monoethyl ether, propylene glycol methyl ether, methyl cellosolve acetate, ethyl cellosolve acetate, diethylene glycol monomethyl ether, diethylene glycol monoethyl ether, propylene glycol methyl ether acetate, propylene glycol propylether acetate, diethylene glycol dimethylether, ethyl lactate, toluene, xylene, methyl ethyl ketone, cyclohexanone, 2-heptanone, 3-heptanone and 4-heptanone.

Yet another aspect of the present invention provides a method of forming a pattern on a substrate. A photoresist film is formed on an object layer by coating the object layer with a photoresist composition including about 7 percent to about 14 percent by weight of a cyclodextrin derivative having a chemical structure represented by the Formula (1), about 0.1 percent to about 0.5 percent by weight of a photoacid generator and a remainder of an organic solvent. The photoresist film is partially exposed to light by performing an exposure process. The photoresist film is developed using a developing solution to form a photoresist pattern on the object layer. The object layer is partially etched using the photoresist pattern as an etching mask to form the pattern on the substrate.

The method of forming the pattern on the substrate may further include heating the photoresist film at a temperature of about 110° C. to about 130° C. before developing the photoresist film. Also, the exposure process may be performed by utilizing an $F_2$ laser, an ArF laser, a KrF laser, an X-ray or an ion beam as a source of the light.

According to aspects of the present invention, the photoresist composition including the cyclodextrin derivative may have an excellent solubility to a developing solution and form a photoresist pattern having a uniform profile. In addition, the photoresist composition may include the cyclodextrin derivative having a toroidal structure, so that the photoresist composition may have advantages originating from a low molecular weight of a building block and an enhanced etching resistance.

BRIEF DESCRIPTION OF THE DRAWINGS

The embodiments of the present invention will be described with reference to the attached drawings, in which.

DETAILED DESCRIPTION OF THE EMBODIMENTS

The present invention will now be described more fully with reference to the accompanying drawings, in which exemplary embodiments of the invention are shown. The invention, however, may be embodied in various different forms, and should not be construed as being limited only to the illustrated embodiments. Rather, these embodiments are provided as examples, to convey the concept of the invention to one skilled in the art. Accordingly, known processes, elements, and techniques are not described with respect to some of the embodiments of the present invention. Throughout the drawings and written description, like reference numerals will be used to refer to like or similar elements. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present. As used herein, the term "and/or" includes any and all combinations of one or more of the associated listed items.

It will be understood that, although the terms first, second, third, etc., may be used to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the spirit and scope of the present invention.

Spatially relative terms, such as "beneath," "below," "lower," "above," "upper" and the like, may be used for ease of description to describe the relationships between elements or features, as illustrated in the figures. It is understood that the spatially relative terms are intended to encompass different orientations of the device in use or operation, in addition to the orientation depicted in the figures. For example, when the device in the figures is turned over, elements described as "below" or "beneath" other elements or features would then be oriented above the other elements or features. Thus, the example term "below" can encompass both an orientation of above and below. The device may be otherwise oriented (rotated 90 degrees or at other orientations) and the spatially relative descriptors are to be interpreted accordingly.

The terminology used herein is for the purpose of describing particular embodiments only, and is not intended to be limiting of the present invention. As used herein, the singular forms "a," "an" and "the" are intended to include the plural forms as well, unless the context clearly indicates otherwise. It is further understood that the terms "comprises" and/or "comprising" specify the presence of stated features, integers, steps, operations, elements and/or components, but do not preclude the presence of one or more additional features, integers, steps, operations, elements, components and/or groups thereof.

Example embodiments of the present invention are described herein with reference to cross-section illustrations that are schematic illustrations of idealized embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated in the figures, but are to include deviations in shapes that result, for example, from manufacturing. For example, an implanted region illustrated as a rectangle for purposes of description, may typically have rounded or curved features and/or a gradient of implant concentration at its edges, as a practical matter, rather than a binary change from implanted to non-implanted regions. Likewise, a buried region formed by implantation may result in some implantation in a region between the buried region and the surface through which the implantation takes place. Thus, the regions illustrated in the figures are schematic in nature and their shapes are not intended to illustrate the actual shape of a region of a device, and are not intended to otherwise limit the scope of the present invention.

Unless otherwise defined, all terms (including technical and scientific terms) used herein have the same meaning as commonly understood by one of ordinary skill in the art. It is further understood that terms, such as those defined in commonly used dictionaries, should be interpreted as having meanings that are consistent with their respective meanings in the context of the relevant art and will not be interpreted in an idealized or overly formal sense, unless expressly so defined herein.

Cyclodextrin Derivative

A cyclodextrin derivative for a photoresist composition according to an embodiment of the present invention includes a β-cyclodextrin moiety, having an adhesion portion, and at least one alkyl carbonate group acting as a protecting group. The cyclodextrin derivative may have the following characteristics.

First, the cyclodextrin derivative has a single molecular weight and a definite molecular structure, and thus there is no distribution of the molecular weight. Second, a building block of a photoresist pattern is a single molecule, so that the corresponding photoresist pattern may have a molecular level resolution. Third, the cyclodextrin derivative included in a photoresist film may provide a large solubility difference between a light-exposed portion and an unexposed portion of the photoresist film in a developing process, so that the photoresist film may be uniformly developed, A molecular interaction, such as a chain entanglement, may not be generated because the cyclodextrin derivative has a small molecular size, a short rotational radius and a complex three-dimensional structure. Fourth, because there is no chain entanglement, a line width roughness of the photoresist pattern may be greatly reduced.

The cyclodextrin derivative includes a β-cyclodextrin moiety and at least one alkyl carbonate group. The cyclodextrin derivative has a chemical structure represented by Formula (1):

Formula (1)

In Formula (1), $R_1$ represents an alkyl group having 1 to 10 carbon atoms. The chemical structure of the cyclodextrin derivative may also be represented by Formula (1-1):

Formula (1-1)

In Formula (1-1), $R_1$ represents an alkyl group having 1 to 10 carbon atoms.

The cyclodextrin derivative may be prepared by combining β-cyclodextrin represented by Formula (2) with tert-alkyl carbonate represented by Formula (3):

Formula (2)

Formula (3)

In the Formula (3), each of $R_2$, $R_3$ and $R_4$ independently represents an alkyl group having 1 to 3 carbon atoms.

The β-cyclodextrin, included in the cyclodextrin derivative and represented by Formula (2), may be a base resin for improving an etching resistance of the photoresist pattern. The alkyl carbonate group introduced in the β-cyclodextrin may act as a protecting group. The protecting group can be detached from the cyclodextrin derivative by reacting with an acid ($H^+$), while being provided with energy.

The cyclodextrin derivative represented by Formula (1) includes a hydroxyl group (OH) acting as an adhesion portion. Particularly, the hydroxyl group (OH) included in the β-cyclodextrin may have a hydrophilic property. The cyclodextrin derivative has a toroidal structure, so that the cyclodextrin derivative may not exhibit crystalline properties that are generally characteristic of a molecular compound, and the cyclodextrin derivative may have amorphous properties. Therefore, the cyclodextrin derivative may be applied to a photoresist composition suitable for spin-coating.

In accordance with an exemplary embodiment of the present invention, the cyclodextrin derivative may be prepared by reacting the β-cyclodextrin, represented by Formula (2), with di-tert-butyl dicarbonate, represented by Formula (4), below:

Formula (4)

Particularly, the β-cyclodextrin and the di-tert-butyl dicarbonate may be input into a reactor containing an organic solvent to react with each other. A tert-butoxycarbonyl group of the di-tert-butyl dicarbonate may be combined with oxygen of the hydroxyl group of the β-cyclodextrin, and thus the cyclodextrin derivative may be obtained. An example of the organic solvent used for preparing the cyclodextrin derivative may include N,N-dimethylacetamide. In addition, a catalyst, such as a pyridine-based compound, may be employed in the reaction for preparing the cyclodextrin derivative. An example of the pyridine-based compound may include 4-(dimethylamino)pyridine.

The cyclodextrin derivative having the above-mentioned chemical structure may be applied to a photoresist composition to form a photoresist pattern having a fine line width and an improved roughness.

Photoresist Composition

A photoresist composition of an exemplary embodiment of the present invention includes the cyclodextrin derivative described above, having a chemical structure represented by Formula (1), a photoacid generator and an organic solvent.

Formula (1)

In Formula (1), $R_1$ represents an alkyl group having 1 to 10 carbon atoms. The chemical structure of the cyclodextrin derivative may also be represented by Formula (1-1):

Formula (1-1)

In Formula (1-1), $R_1$ likewise represents an alkyl group having 1 to 10 carbon atoms.

When the photoresist composition includes less than about 7 percent by weight of the cyclodextrin derivative based on a total weight of the photoresist composition, the photoresist pattern may have a poor etching resistance, so the photoresist pattern may not be used for etching an object layer. In addition, when the amount of the cyclodextrin derivative is greater than about 14 percent by weight based on the total weight of the photoresist composition, it may be difficult to form a photoresist film having a substantially uniform thickness on the object layer. Therefore, the photoresist composition may include about 7 percent to about 14 percent by weight of the cyclodextrin derivative. For example, when the photoresist composition is applied to form a photoresist pattern having a line width less than about 80 nm, the photoresist composition may include about 9 percent to about 12 percent by weight of the cyclodextrin derivative.

The cyclodextrin derivative represented by Formula (1) includes a β-cyclodextrin moiety having an adhesion portion and at least one alkyl carbonate group acting as a protecting group. The β-cyclodextrin represented by the Formula (2) includes a hydroxyl group having hydrophilicity, and the alkyl carbonate group has a chemical structure represented, for example, by Formula (3).

The cyclodextrin derivative having the above-mentioned chemical structure has a toroidal structure, so that the cyclodextrin derivative may improve an etching resistance of a photoresist pattern formed using the photoresist composition. In addition, the cyclodextrin derivative may not exhibit crystalline properties that are generally characteristic of a molecular compound, and may have amorphous properties. Therefore, the cyclodextrin derivative may be applied to a photoresist composition suitable for spin-coating. The cyclodextrin derivative represented by Formula (1) has been previously described, above, so any further explanation will not be repeated herein.

In the photoresist composition according to an exemplary embodiment of the present invention, a certain quantity of an acid ($H^+$) and heat may be required to detach the protecting group from the cyclodextrin derivative represented by Formula (1). The acid may be generated from a photoacid generator included in the photoresist composition. The photoacid generator is a material that may generate an acid when exposed to light.

When the photoresist composition has less than about 0.1 percent by weight of the photoacid generator based on a total weight of the photoresist composition, the acid ($H^+$) may not be sufficiently generated, which may deteriorate an ability to detach the protecting group from the cyclodextrin derivative in an exposure process. In addition, when the amount of the photoacid generator is greater than about 0.5 percent by weight, the acid may be overproduced in the exposure process, and thus a photoresist film may be excessively developed and/or a top loss of a photoresist pattern may be generated in a developing process. Therefore, the photoresist composition may include about 0.1 percent to about 0.5 percent by weight of the photoacid generator, and preferably about 0.2 percent to about 0.4 percent by weight of the photoacid generator.

Examples of the photoacid generator that may be applied to the photoresist composition may include a triarylsulfonium salt, a diaryliodonium salt, a sulfonate, N-hydroxysuccinimide triflate, etc. These exemplary photoacid generators may be used alone or in any mixture thereof. More specific examples of the photoacid generator may include triphenylsulfonium triflate, triphenylsulfonium antimony salt, diphenyliodonium triflate, diphenyliodonium antimony salt, methoxydiphenyliodonium triflate, di-tert-butyldiphenyliodonium triflate, 2,6-dinitrobenzyl sulfonate, pyrogallol tris(alkylsulfonate), norbornene dicarboximide triflate, triphenylsulfonium nonaflate, diphenyliodonium nonaflate, methoxydiphenyliodonium nonaflate, di-tert-butyldiphenyliodonium nonaflate, N-hydroxysuccinimide nonaflate, norbornene dicarboximide nonaflate, triphenylsulfonium perfluorooctanesulfonate, diphenyliodonium perfluorooctanesulfonate, methoxyphenyliodonium perfluorooctanesulfonate, di-tert-butyldiphenyliodonium triflate, N-hydroxysuccinimide perfluorooctanesulfonate, norbornene dicarboximide perfluorooctanesulfonate, etc., which can be used alone or in any mixture thereof.

Examples of the organic solvent that may be used in the photoresist composition may include ethylene glycol monomethyl ether, ethylene glycol monoethyl ether, propylene glycol methyl ether, methyl cellosolve acetate, ethyl cellosolve acetate, diethylene glycol monomethyl ether, diethylene glycol monoethyl ether, propylene glycol methylether acetate, propylene glycol propylether acetate, diethylene glycol dimethyl ether, ethyl lactate, toluene, xylene, methyl ethyl ketone, cyclohexanone, 2-heptanone, 3-heptanone, 4-heptanone, etc. These can be used alone or in any mixtures thereof.

In an exemplary embodiment of the present invention, the photoresist composition may further include an additive in order to improve photoresist characteristics. Examples of the additive may include an organic base and a surfactant. The organic base may prevent an airborne alkali compound, such as an amine, from influencing the photoresist pattern obtained after the exposure process, and thus the organic base may maintain or adjust a shape of the photoresist pattern. Examples of the organic base that may be used in the photoresist composition may include triethylamine, triisobutylamine, triisooctylamine, triisodecylamine, diethanolamine, triethanolamine, etc., which can be used alone or in any mixtures thereof.

The surfactant may improve a coatability of the photoresist composition and inhibit a striation on a photoresist film formed using the photoresist composition. Examples of the surfactant that may be used in the photoresist composition may include fluorine-containing surfactants, such as those available under the trade names SURFLON SC-103, SR-100 (manufactured by Asahi Glass Co., Ltd.), EF-361 (manufactured by Tohoku Hiryou K.K.), FLORAD Fc-431, Fc-135, Fc-98 and Fc-176 (manufactured by Sumitomo 3M Ltd.), etc. These exemplary surfactants are commercially available.

Method of Forming a Pattern

FIGS. 1 to 4 are cross-sectional views illustrating a method of forming a pattern, in accordance with an exemplary embodiment of the present invention.

Figure 1:
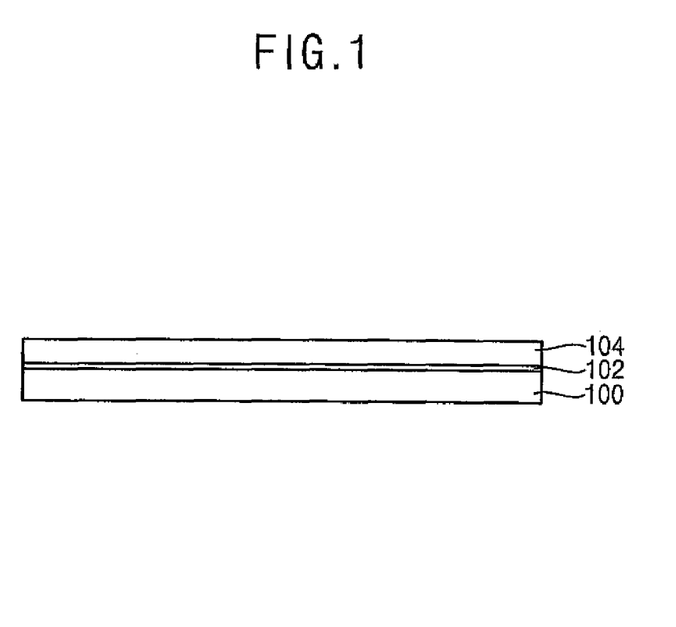
FIGS. 1 to 4 are cross-sectional views illustrating a method of forming a pattern, in accordance with an exemplary embodiment of the present invention.

Referring to FIG. 1, an etching object is prepared. The etching object may include, for example, a semiconductor substrate 100 and a thin film 102 formed on the semiconductor substrate 100. An exemplary case in which the etching object includes a thin film 102 will be described hereinafter. Examples of the thin film 102 may include a silicon nitride film, a polysilicon film, a silicon oxide film, etc.

After rinsing the surface of the thin film 102 to remove contaminants from the thin film 102, a photoresist film 104 may be formed on the thin film 102 (e.g., an object layer) by coating the thin film 102 with a photoresist composition including a cyclodextrin derivative that has a chemical structure represented by Formula (1), a photoacid generator and an organic solvent. The cyclodextrin derivative represented by the Formula (1) and the photoresist composition including the cyclodextrin derivative are described above, so the explanations will not be repeated.

The semiconductor substrate 100 on which the photoresist film 104 is formed may be thermally treated in a first baking process. The first baking process may be performed, for example, at a temperature of about 90° C. to about 120° C. In the first baking process, adhesiveness between the photoresist film 104 and the thin film 102 may be enhanced.

Figure 2:
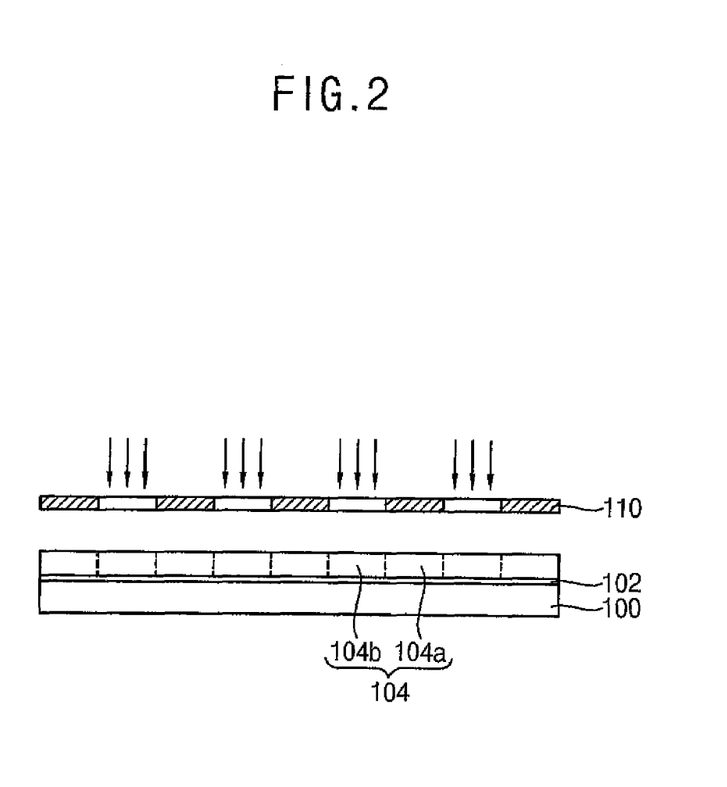

Referring to FIG. 2, the photoresist film 104 is partially exposed to light during an exposure process, according to an exemplary embodiment of the present invention. In particular, a mask 110 having a predetermined pattern may be positioned on a mask stage of an exposure apparatus, and then the mask 110 is aligned over the photoresist film 104. A portion of the photoresist film 104 formed on the substrate 100 may be selectively reacted with light transmitted through the mask 110 while the light is irradiated on the mask 110 for a predetermined time. Examples of the light that may be used in the exposure process may include an ArF laser having a wavelength of about 193 nm, a KrF laser having a wavelength of about 248 nm, an $F_2$ laser, an Hg—Xe light, an X-ray, an ion beam, etc.

An exposed portion 104b of the photoresist film 104 may be more hydrophilic than an unexposed portion 104a of the photoresist film 104. Accordingly, the exposed portion 104b and the unexposed portion 104a of the photoresist film 104 have different solubilities.

Subsequently, a second baking process may be performed on the semiconductor substrate 100. The second baking process may be performed, for example, at a temperature of about 90° C. to about 150° C. During the second baking process, the exposed portion 104b of the photoresist film 104 may become soluble in a developing solution.

Figure 3:
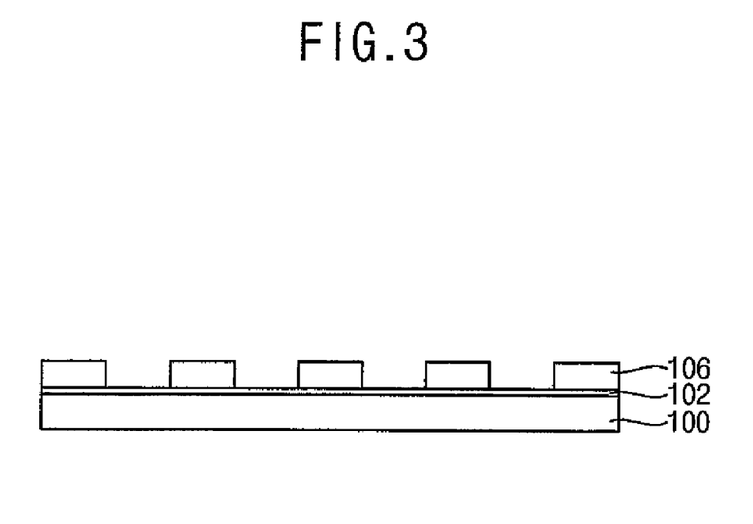

Referring to FIG. 3, a photoresist pattern 106 is formed by dissolving the exposed portion 104b of the photoresist film 104 in a developing solution and then by removing the exposed portion 104b from the photoresist film 104.

Particularly, the exposed portion 104b of the photoresist film 104 may be removed by dissolving the exposed portion 104b of the photoresist film 104 using an aqueous solution of tetramethylammonium hydroxide, for example, as the developing solution. The hydrophilicities of the unexposed and exposed portions 104a and 104b of the photoresist film 104, respectively, are different from each other, and thus the exposed portion 104b of the photoresist film 104 may be easily removed by being dissolved in the developing solution, to provide the photoresist pattern 106. Subsequently, the semiconductor substrate 100 having the photoresist pattern 106 may be rinsed and dried, completing the photoresist pattern 106.

The photoresist composition includes the cyclodextrin derivative, having a molecular weight less than or equal to about 1800. Accordingly, a deviation of line width roughness in the photoresist pattern 106 may be less than about 14 percent, based on both edges of a line.

Figure 4:
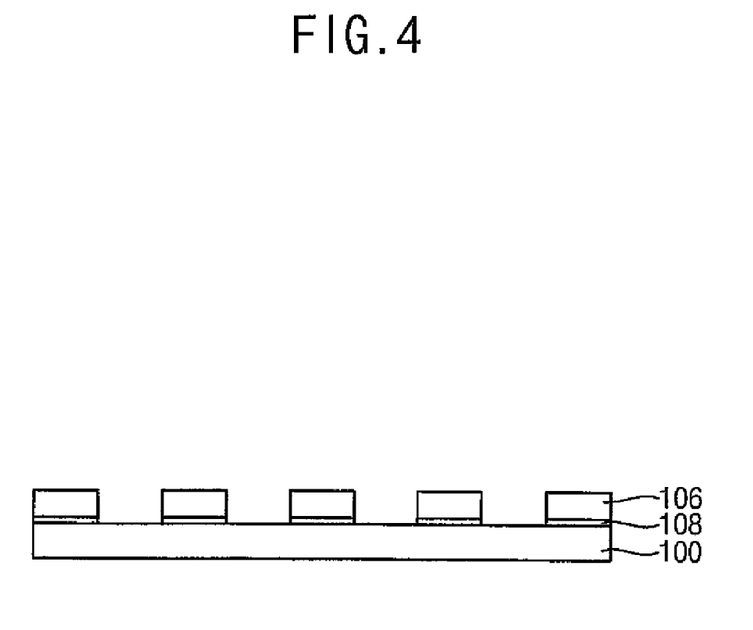

Referring FIG. 4, the thin film 102 is partially etched using the photoresist pattern 106 as an etching mask to form a thin film pattern 108 on the substrate.

Embodiments of the present invention will be further described through examples of preparing a cyclodextrin derivative and a photoresist composition including the cyclodextrin derivative, below. The present invention may, however, be embodied in many different forms and should not be construed as limited to examples set forth herein.

EXAMPLE 1

Synthesis of Cyclodextrin Derivative

About 14.8 g, i.e., 0.013 moles, of β-cyclodextrin was dissolved in about 20 mL of N,N-dimethylacetamide, and then 4-(dimethylamino)pyridine was added to the solution as a catalyst. While keeping the solution at about 0° C., about 17.46 g, i.e., about 18.28 mL or about 0.080 moles, of di-tert-butyl dicarbonate was slowly added to the solution. The solution was reacted for about twelve hours while slowly increasing the temperature of the solution up to about 25° C. or room temperature. A white solid material was precipitated by dropwise addition of the obtained solution to distilled water. A final product was filtered from the aqueous solution including the white solid material and dried. As a result, a cyclodextrin derivative including β-cyclodextrin, in which a tert-butyl carbonate group was combined, was obtained.

A structure of the final product was confirmed using a $^1$H-nuclear magnetic resonance ($^1$H-NMR) spectrum. The $^1$H-NMR spectrum was obtained using chloroform-d (CDCl$_3$) as a solvent and a 300 MHz NMR spectrometer. The $^1$H-NMR spectrum showed chemical shifts (δ) of the final product at 1.45 (3H, s, methyl), 3.8 (m, H from β-cyclodextrin), 4.8 (broad s, primary-OH) and 5.0 (broad s, secondary-OH).

EXAMPLE 2

Preparation of a Photoresist Composition

Preparation of a Photoresist Composition was Performed in a Laboratory in which a far ultraviolet ray was blocked. About 111 parts by weight of the cyclodextrin derivative obtained in Example 1 and about 20 parts by weight of triphenylsulfonium triflate used as a photoacid generator were dissolved in about 887 parts by weight of propyleneglycol monomethyl ether acetate. The solution was then filtered using a membrane filter having a pore size of about 0.2 μm. As a result, a photoresist composition was obtained.

Evaluation of a Photoresist Pattern

The photoresist composition prepared in Example 2 was spin-coated on a silicon wafer, and then the silicon wafer was heated at a temperature of about 100° C. for about 90 seconds. As a result, a photoresist film having a thickness of about 0.4 μm was formed on the silicon wafer. The photoresist film was partially exposed to an Hg—Xe laser, and then the photoresist film was thermally treated again at a temperature of about 110° C. for about 90 seconds.

An exposed portion of the photoresist film was removed from the photoresist film using about 2.38 percent by weight of a tetramethylammonium hydroxide developing solution. A rinse process and a dry process were then performed on the silicon wafer to remove residues of the developing solution to complete a photoresist pattern. A picture of the photoresist pattern formed on the silicon wafer is shown in FIG. 5.

Figure 5:
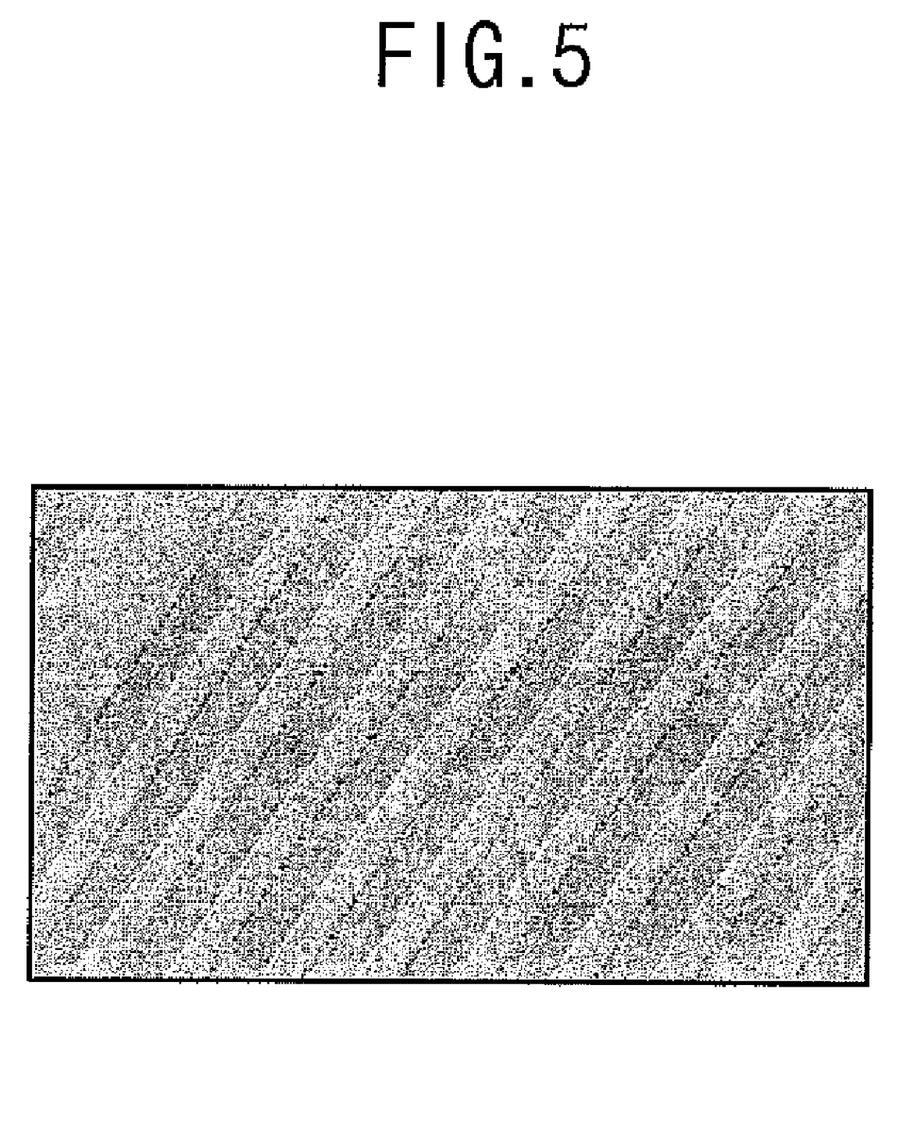
FIG. 5 is an image showing a photoresist pattern formed using a photoresist composition, in accordance with an exemplary embodiment of the present invention.

FIG. 5 is a picture showing a photoresist pattern formed by using a photoresist composition in accordance with an exemplary embodiment of the present invention. Referring to FIG. 5, the photoresist pattern formed using the above-mentioned photoresist composition has a uniform line width of about 0.8 μm and an excellent profile.

The cyclodextrin derivative may not exhibit crystalline properties, which are generally characteristics of a low molecular weight compound, and may have amorphousness. The cyclodextrin derivative may therefore be applied to a photoresist composition suitable for spin-coating. The photoresist composition includes the cyclodextrin derivative having a toroidal structure, so that the photoresist composition may have advantages originating from a low molecular weight of a building block and may form a photoresist pattern having a uniform profile.

In addition, the photoresist composition may form a photoresist pattern having an enhanced etching resistance compared to a conventional photoresist composition that includes a molecular compound of a low molecular weight. Accordingly, a photoresist pattern having an improved profile may be formed, and efficiency of a semiconductor device may be increased.

Photoresist compositions according to exemplary embodiments of the present invention include a compound having a low molecular weight to be used as a building block, instead of the polymer. The photoresist composition may have an enhanced solubility to a developing solution, as compared to a conventional polymer-based photoresist composition, and may form a photoresist pattern having a uniform profile.

The foregoing is illustrative of the present invention and is not to be construed as limiting thereof. While the present invention has been described with reference to exemplary embodiments, it will be apparent to those skilled in the art that various changes and modifications may be made without departing from the spirit and scope of the present invention. Therefore, it should be understood that the above embodiments are not limiting, but illustrative. Accordingly, all such modifications are intended to be included within the scope of the present invention, as defined in the claims.

What is claimed is:

1. The cyclodextrin derivative for a photoresist comprising: a β-cyclodextrin moiety; and at least one alkyl carbonate group, wherein the cyclodextrin derivative has a chemical structure represented by Formula (1),

Formula (1)

wherein $R_1$ represents an alkyl group comprising 1 to 10 carbon atoms.

2. The cyclodextrin derivative for a photoresist comprising: a βcyclodextrin moiety; and at least one alkyl carbonate group, wherein the cyclodextrin derivative is prepared by combining β-cyclodextrin represented by Formula (2) with a tert-alkyl carbonate represented by Formula (3),

Formula (2)

Formula (3)

wherein in the Formula (3), each of $R_2$, $R_3$ and $R_4$ independently represents an alkyl group comprising 1 to 3 carbon atoms.

3. The cyclodextrin derivative for a photoresist comprising: a β-cyclodextrin moiety; and at least one alkyl carbonate group, wherein the cyclodextrin derivative is prepared by reacting β-cyclodextrin with di-tert-butyl dicarbonate, represented by Formula (4), in an organic solvent Formula (4)

4. A photoresist composition comprising:
about 7 percent to about 14 percent by weight of a cyclodextrin derivative having a chemical structure represented by Formula (1);
about 0.1 percent to about 0.5 percent by weight of a photoacid generator; and
a remainder of an organic solvent,

Formula (1)

wherein $R_1$ represents an alkyl group comprising 1 to 10 carbon atoms.

5. The photoresist composition of claim 4, wherein the cyclodextrin derivative is prepared by combining β-cyclodextrin represented by Formula (2) with a tert-alkyl carbonate represented by Formula (3),

Formula (2)

Formula (3)

wherein in the Formula (3), each of $R_2$, $R_3$ and $R_4$ independently represents an alkyl group comprising 1 to 3 carbon atoms.

6. The photoresist composition of claim 4, wherein the cyclodextrin derivative is prepared by reacting β-cyclodextrin with di-tert-butyl dicarbonate represented by Formula (4) in the organic solvent Formula (4)

Formula (1)

wherein $R_1$ represents an alkyl group having 1 to 10 carbon atoms;
- partially exposing the photoresist film to light by performing an exposure process;
- developing the photoresist film using a developing solution to form a photoresist pattern on the object layer; and
- partially etching the object layer using the photoresist pattern as an etching mask to form the pattern on the substrate.

10. The method of claim 9, further comprising:
heating the photoresist film at a temperature of about 110° C. to about 130° C. before developing the photoresist film.

11. The method of claim 9, wherein the exposure process is performed by utilizing an $F_2$ laser, an ArF laser, a KrF laser, an X-ray or an ion beam as a source of the light.

* * * * *

7. The photoresist composition of claim 4, wherein the photoacid generator comprises at least one selected from the group consisting of a triarylsulfonium salt, a diaryliodonium salt, a sulfonate and N-hydroxysuccinimide triflate.

8. The photoresist composition of claim 4, wherein the organic solvent comprises at least one selected from the group consisting of ethylene glycol monomethyl ether, ethylene glycol monoethyl ether, propylene glycol methyl ether, methyl cellosolve acetate, ethyl cellosolve acetate, diethylene glycol monomethyl ether, diethylene glycol monoethyl ether, propylene glycol methyl ether acetate, propylene glycol propylether acetate, diethylene glycol dimethylether, ethyl lactate, toluene, xylene, methyl ethyl ketone, cyclohexanone, 2-heptanone, 3-heptanone and 4-heptanone.

9. A method of forming a pattern on a substrate, the method comprising:
forming a photoresist film on an object layer by coating the object layer with a photoresist composition comprising about 7 percent to about 14 percent by weight of a cyclodextrin derivative having a chemical structure represented by Formula (1), about 0.1 percent to about 0.5 percent by weight of a photoacid generator, and a remainder of an organic solvent,